United States Patent
Nemechek (10) Patent No.: US 10,335,396 B2
(45) Date of Patent: Jul. 2, 2019

(54) METHODS OF REVERSING AUTONOMIC NERVOUS SYSTEM DAMAGE

(71) Applicant: Patrick M. Nemechek, Buckeye, AZ (US)

(72) Inventor: Patrick M. Nemechek, Buckeye, AZ (US)

( * ) Notice: Subject to any disclaimer, the term of this patent is extended or adjusted under 35 U.S.C. 154(b) by 1 day.

(21) Appl. No.: 15/336,518

(22) Filed: Oct. 27, 2016

(65) Prior Publication Data

US 2018/0117017 A1    May 3, 2018

(51) Int. Cl.
| | |
|---|---|
| A61N 1/04 | (2006.01) |
| A61K 31/437 | (2006.01) |
| A61K 31/202 | (2006.01) |
| A61K 31/201 | (2006.01) |
| A61K 36/63 | (2006.01) |
| A61N 1/36 | (2006.01) |

(52) U.S. Cl.
CPC .......... *A61K 31/437* (2013.01); *A61K 31/201* (2013.01); *A61K 31/202* (2013.01); *A61K 36/63* (2013.01); *A61N 1/0456* (2013.01); *A61N 1/36014* (2013.01); *Y02A 50/385* (2018.01); *Y02A 50/411* (2018.01)

(58) Field of Classification Search
CPC .................................................. A61N 1/0456
See application file for complete search history.

(56) References Cited

U.S. PATENT DOCUMENTS

| | | | |
|---|---|---|---|
| 6,838,471 B2 | 1/2005 | Tracey | |
| 7,079,888 B2 | 7/2006 | Dung et al. | |
| 7,499,748 B2 | 3/2009 | Moffitt et al. | |
| 7,529,579 B2 | 5/2009 | Colombo et al. | |
| 8,676,324 B2 | 3/2014 | Simon et al. | |
| 8,706,223 B2 | 4/2014 | Zhou et al. | |
| 8,788,034 B2 | 7/2014 | Levine et al. | |
| 8,868,177 B2 | 10/2014 | Simon et al. | |
| 8,914,114 B2 | 12/2014 | Tracey et al. | |
| 9,162,064 B2 | 10/2015 | Faltys et al. | |
| 9,211,409 B2 | 12/2015 | Tracey et al. | |
| 9,211,410 B2 | 12/2015 | Levine et al. | |
| 9,414,219 B2 | 8/2016 | Shao et al. | |
| 9,415,220 B1 * | 8/2016 | Spinelli | A61N 1/36032 |
| 9,457,187 B2 | 10/2016 | Zhao et al. | |

OTHER PUBLICATIONS

Nemechek, Paul, "Fatty Liver or NAFLD—What is Fatty Liver?" Apr. 21, 2011 https://www.nemecheckconsultativemedicine.com/blog/fatty-liver-or-nafld/.*

(Continued)

*Primary Examiner* — Eric D. Bertram
(74) *Attorney, Agent, or Firm* — Procopio, Cory, Hargreaves & Savitch LLP (57) ABSTRACT

Provided herein are methods for preventing, reducing or reversing acute and/or chronic autonomic damage by the suppression of pro-inflammatory cytokines in a subject in need thereof, which methods comprise administering to said subject an effective amount of an antibiotic; polyunsaturated omega-3 fatty acid; and oleic acid; providing VNS (vagal nerve stimulation) to the subject; and placing said subject on an intermittent fasting regimen.

15 Claims, 6 Drawing Sheets

(56) References Cited

OTHER PUBLICATIONS

Nemechek, Paul, "Fish Oil and Flax Improves Your Metabolism," Nov. 3, 2013, https://www.nemecheckconsultativemedicine.com/blog/fish-oil-and-flax-improves-your-metabolism/.*

Nemechek, Paul, "Breakfast is Not Your Friend," Aug. 7, 2015, https://www.nemecheckconsultativemedicine.com/blog/breakfast-is-not-your-friend/.*

Nemechek, Paul, "Inflammation and Depression," 2014, https://www.nemecheckconsultativemedicine.com/blog/inflammation-and-depression-new-answers/.*

Nemechek, Paul, "Olive Oil Tastes Like 'Skinny Jeans'," Aug. 30, 2014, https://www.nemecheckconsultativemedicine.com/blog/olive-oil-tastes-like-skinny-jeans/.*

Guixiang Zhao, "Dietary α-linolenic acids inhibits proinflammatory cytokine production by peripheral blood monouclear cells in hypercholesterolemic subjects," Am J Clin Nutr 2007;85:385-91, 2007 American Society for Nutrition.

Simon C. Dyall, "Long-chain omega-3 fatty acids and the brain: A review of the independent and shared effects of EPA, DPA and DHA," Frontiers in Aging Neuroscience, Apr. 2015.

George E. Billman, "Effect of dietary omega-3 polyunsaturated fatty acids on heart rate and heart rate variability in animals susceptible or resistant to ventricular fibrillation," Frontiers in Physiology, Mar. 2012, vol. 3.

Wu A, "Dietary strategy to repair plasma membrane after brain trauma: implications for plasticity and cognition," Neurorehabil Neural Repair, Aug. 2013.

Kazuhiro Tanaka, "Effects of docosahexaenoic acid on neurotransmission", Biomolecules & Therapeutics 20(2), 152-157 (2012).

Jeppe Hagstrup Christensen, "Omega-3 polyunsaturated fatty acids and heart rate variability," Frontiers in Physiology, Nov. 2011, vol. 2, Article 84.

Barbara S. Beltz, "Omega-3 fatty acids upregulate adult neurogenesis," NIH Public Access Author Manuscript, Neurosci Lett. Mar. 26, 2007; 415(2): 154-158.

"Omega-3 fatty acids supplementation restores mechanisms that maintain brain homeostasis in traumatic brain injury," Abstract.

Miki Igarashi, "Dietary N-6 polyunsaturated fatty acid deprivation increases docosahexaenoic acid metabolism in rat brain," J Neurochem Mar. 2012; 120(6): 985-997.

Nicolas Blondeau, "Subchronic alpha-linolenic acid treatment enhances brain plasticity and exerts an antidepressant effect: a versatile potential therapy for stroke," Neuropsychopharmacology: official publication of the American College of Neuropsychopharmacology, Aug. 2009.

Bronwen Martin, "Caloric restriction and intermittent fasting: Two potential diets for successful brain aging," Ageing Res Rev. Aug. 2006; 5(3); 332-353.

Ameer Y. Taha, "Dietary omega-6 fatty acid lowering increases bioavailability of omega-3 polyunsaturated fatty acids in human plasma lipid pools," Prostaglandins Leukot Essent Fatty Acids, May 2014; 90(5): 151-157.

Xiao-Guang Luo, "The changing phenotype of microglia from homeostasis to disease," Lou and Chen Translational Neurodegeneration 2012, 1:9.

Marwan A. Maalouf, "The neuroprotective properties of calorie restriction, the ketogenic diet, and ketone bodies," Brain Res Rev. Mar. 2009; 59(2): 293-315.

Christopher T. Ford, "Identification of (poly)phenol treatments that modulate the release of pro-inflammatory cytokines by human lymphocytes," British Journal of Nutrition (2016), 1699-1710.

Shannon Levesque, "Diesel exhaust activates and primes microglia: Air pollution, neuroinflammation, and regulation of dopaminergic neurotoxicity," Environmental Health Perspectives, vol. 119, No. 8, Aug. 2011.

Andre C., "Diet-induced obesity progressively alters cognition, anxiety-like behavior and lipopolysaccharide-induced depressive-like behavior: Focus on brain indoleamine 2,3-dioxygenase activation," Brain Behav Immun. Oct. 2014; 41: 10-21.

Christine M. Sandiego, "Imaging robust microglial activation after lipopolysaccharide administration in humans with PET," PNAS, Oct. 6, 2015, 12468-12473, vol. 112, No. 40.

Dennys E. Cintra "Unsaturated fatty acids revert diet-induced hypothalamic inflammation in obesity," PloS ONE, Jan. 2012, vol. 7, Issue 1.

Anthony F. Domenichiello, "Whole body synthesis rates of DHA from ∝-linolenic acid are greater than brain DHA accretion and uptake rates in adult rats," Journal of Lipid Research, vol. 55, 2014.

Philip K-Y Chang, "Docosahexaenoic acid (DHA): A modulator of microglia activity and dendritic spine morphology," Journal of Neuroinflammation (2015) 12:34.

Lloyd D. Harvey, "Administration of DHA reduces endoplasmic reticulum stress-associated inflammation and alters microglial or macrophage activation in traumatic brain injury," ASN Neuro Nov.-Dec. 2015: 1-15.

Imanuel Lerman, "Noninvasive transcutaneous vagus nerve stimulation decreases whole blood culture-derived cytokines and chemokines: a randomized, blinded, health control pilot trial," Neuromodulation, Mar. 2016.

Colm Cunningham, "Microglia and Neurodegeneration: The role of systemic inflammation," GLIA 61:71-90, (2013).

J. Thomas Brenna, "α-Linolenic acid supplementation and conversion to n-3 long chain polyunsaturated fatty acids in humans," ISSFAL Official Statement No. 5.

Zhenying Han, "Activation of α-7 nicotinic acetylcholine receptor reduces ischemic stroke injury through reduction of pro-inflammatory macrophages and oxidative stress," PLOS One, Aug. 2014, vol. 9, Issue 8.

Margaret F. Gregor, "Inflammatory mechanisms in obesity," Annu. Rev. Immunol. 2011, 29:415-445.

Trent Grundy, "Long-term omega-3 supplementation modulates behavior hippocampal fatty acid concentration, neuronal progenitor proliferation and central TNF-∝ expression in 7 month old unchallenged mice," Frontiers in Cellular Neuroscience, Nov. 2014, vol. 8, Article 399.

Pnina Green, "Pathways of polyunsaturated fatty acid utilization: Implications for brain function in neuropsychiatric health and disease," Brain Research, Dec. 2014.

Andrea R. Vasconcelos, "Intermittent fasting attenuates lipopolysaccharide-induced neuroinflammation and memory impairment," Journal of Neuroinflammation, 2014, 11:85.

Diana M. Norden, "Microglia of the aged brain: Primed to be activated and resistant to regulation," Neuropathol Appl. Neurobiol. Feb. 2013; 39(1): 19-34.

* cited by examiner

METHODS OF REVERSING AUTONOMIC NERVOUS SYSTEM DAMAGE

TECHNICAL FIELD

The invention relates to methods for reversing acute and/or chronic autonomic damage by the suppression of pro-inflammatory cytokines.

INTRODUCTION

The automatic nervous system (ANS) regulates "involuntary" organs. The ANS includes the sympathetic nervous system and the parasympathetic nervous system. The sympathetic nervous system is affiliated with stress and the "fight or flight response" to emergencies. The parasympathetic nervous system is affiliated with relaxation and the "rest and digest response." The ANS maintains normal internal homeostasis and works with the somatic nervous system. Autonomic balance reflects the relationship between parasympathetic and sympathetic activity.

Vertebrates achieve internal homeostasis during infection or injury by balancing the activities of proinflammatory and anti-inflammatory pathways. However, in many disease conditions, this internal homeostasis becomes out of balance. For example, endotoxin (lipopolysaccharide, LPS) produced by all Gram-negative bacteria activates macrophages to release cytokines that are potentially lethal.

Inflammation and other deleterious conditions (such as septic shock caused by endotoxin exposure) are often induced by pro-inflammatory cytokines, such as tumor necrosis factor (TNF; also known as TNF-alpha or cachectin), interleukin (IL)-1.alpha., IL-1.beta., IL-6, IL-8, IL-18, interferon, platelet-activating factor (PAF), macrophage migration inhibitory factor (MIF), and other compounds. These pro-inflammatory cytokines are produced by several different cell types, and contribute to various diseases and disorders through their release during an inflammatory cytokine cascade.

Accordingly, there is a need in the art for suppressing the production of pro-inflammatory cytokines from each of their various sources.

SUMMARY

Provided herein are the Nemechek Protocol methods for preventing, reducing or reversing acute and/or chronic autonomic damage by the suppression of pro-inflammatory cytokines in a subject in need thereof, which methods comprise administering to said subject an effective amount of an antibiotic; an effective amount of polyunsaturated omega-3 fatty acid; and an effective amount of oleic acid; providing VNS (vagal nerve stimulation) to the subject; and placing said subject on an intermittent fasting regimen. The invention methods are useful for reducing the levels of pro-inflammatory cytokines within the central nervous system such that natural repair mechanisms are activated and autonomic nervous system function recovers. Such reduction in the levels of pro-inflammatory cytokines within the central nervous system is also useful for treating a variety of neuroinflammatory diseases and/or conditions including traumatic brain injury, concussion, chronic traumatic encephalopathy (CTE), post-concussion syndrome (PCS), Alzheimer's disease, Parkinson's disease, essential tremor, post-traumatic stress disorder (PTSD), chronic depression, treatment resistant epilepsy, autism, developmental delay and sensory perception disorder.

INCORPORATION BY REFERENCE

Herein, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

DETAILED DESCRIPTION

Provided herein are methods for preventing, reducing or reversing acute and/or chronic autonomic damage by the suppression of pro-inflammatory cytokines in a subject in need thereof, which methods comprise administering to said subject an effective amount of an antibiotic; an effective amount of polyunsaturated omega-3 fatty acid; and an effective amount of oleic acid; providing VNS (vagal nerve stimulation) to the subject; and placing said subject on an intermittent fasting regimen. These invention methods are also referred to herein collectively as the Nemechek Protocol, and these methods are useful for treating and/or reversing various disease states that are mediated by autonomic damage caused by pro-inflammatory cytokines.

Generally speaking, the Nemechek Protocol methods of treatment set forth herein reverse autonomic nervous system damage through a combination of supplements, vitamins, chemical compounds, pharmaceutical agents, dietary restrictions and neuromodulation of the vagus nerve, and the like. The combined effect of these treatments is to substantially reduce the levels of pro-inflammatory cytokines within the central nervous system such that natural repair mechanisms are activated and autonomic nervous system function recovers. Autonomic recovery is detected by sequential spectral analysis monitoring of the autonomic nervous system. If no recovery is initially noted, the treatment regimen can be supplemented further.

The invention Nemechek Protocol methods provided herein are believed to be safe, non-invasive, portable, and do not require certified technicians. The invention methods are extremely effective for recovery of autonomic function from a variety of neuroinflammatory conditions including traumatic brain injury, concussion, chronic traumatic encephalopathy (CTE), post-concussion syndrome (PCS), Alzheimer's disease, Parkinson's disease, essential tremor, post-traumatic stress disorder (PTSD), chronic depression, treatment resistant epilepsy, autism, developmental delay, sensory perception disorder, and the like.

In certain embodiments, the present invention methods relate to the reversal of acute and chronic autonomic damage by the suppression of pro-inflammatory cytokines, namely interleukin-1 (IL-1), interleukine-6 (IL-6) and tumor necrosis factor-alpha (TNF-alpha). The pro-inflammatory cytokines are reduced through the cumulative effect of reversing intestinal bacterial overgrowth, normalizing dietary intake of omega-6 and omega-3 fatty acids, supplementation with oleic acid, intermittent restriction of caloric intake, and stimulation of the acetylcholine inflammatory reflex by transcutaneous vagal nerve stimulation (tVNS). If this proves initially inadequate, additional steps to reduce pro-inflammatory cytokines include supplementation with curcumin and/or the introduction of carbohydrate restriction and/or intermittent fasting.

The accurate measurement of pro-inflammatory cytokines within the central nervous system is believed to be unavailable in the clinical setting so recovery of autonomic function as measured by spectral analysis is used herein as a surrogate marker for cytokine suppression and normalization of natural repair mechanisms. If cytokine concentrations are reduced to a healthy physiological range, normal repair mechanisms are activated (i.e., phenotypic shift of microglia to the reparative, restorative M2-phenotype, and increased progenitor stem cell production and functionality), recovery of autonomic strength and function as measured by spectral analysis returns to normal.

Sequential testing of the autonomic nervous system with spectral analysis is particularly preferred in the recovery process because the detection of a reduction in inflammation within the peripheral circulation does not mean there is improvement within the central nervous system. The reduction in pro-inflammatory cytokines within the blood stream may correlate with symptomatic improvements but has little impact on restoring autonomic nervous system function. This is a common scenario in the recovery from minor traumatic brain injuries, commonly referred to as a concussion.

Figure 3:
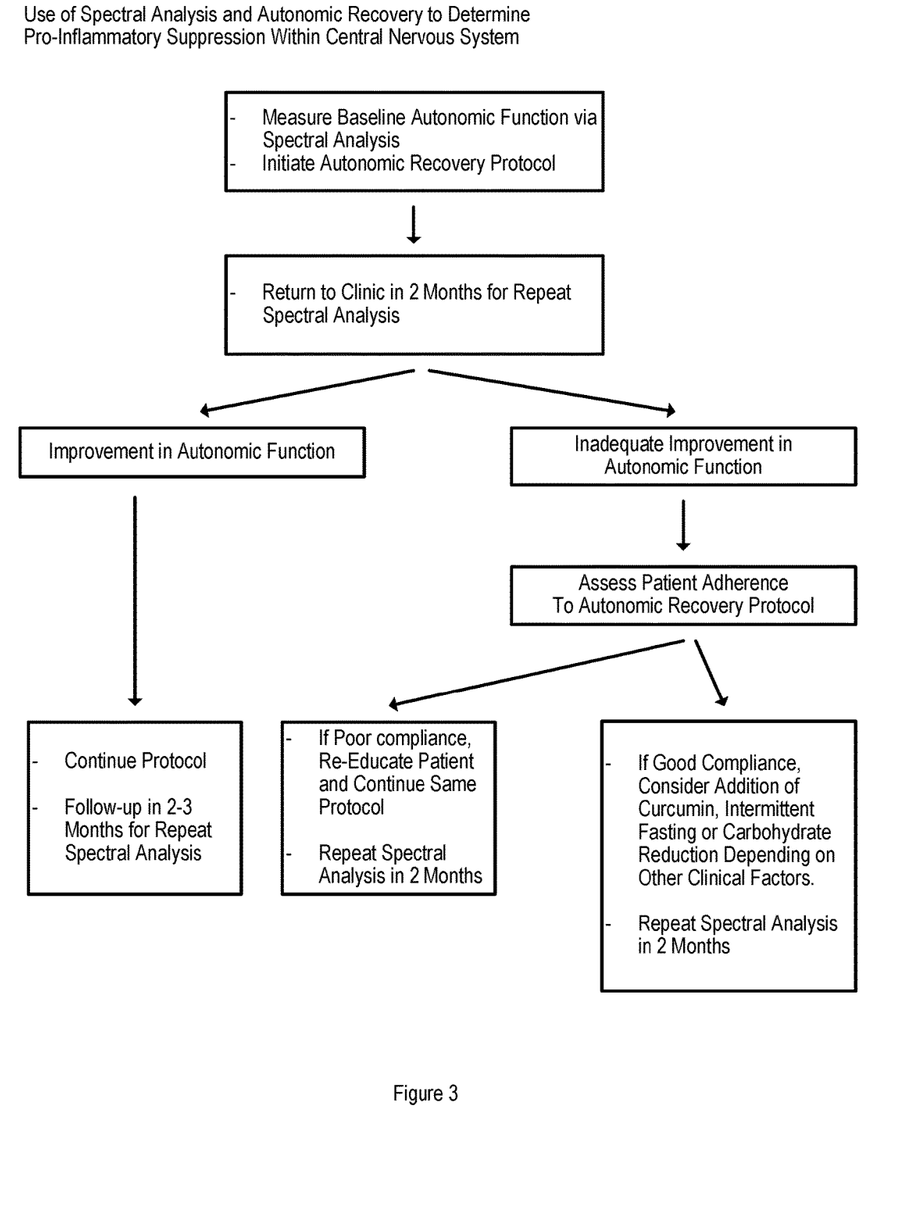
FIG. 3 shows the Use of Spectral Analysis and Autonomic Recovery to Determine Pro-Inflammatory Suppression Within the Central Nervous System.

Prior to initiating the invention Nemechek Protocol methods set forth herein, the subject is sequentially monitored to ascertain the base-level of autonomic nervous system health via spectral analysis. In one embodiment, monitoring of autonomic function via spectral analysis is performed at baseline and again every 1-3 months depending on the severity of the patient's condition, their clinical status, and overall rate of recovery (see FIG. 3). Because the measurement of neuroinflammation from pro-inflammatory cytokines (i.e., IL-1, IL-6, TNF-alpha, INF-gamma) is unavailable in the clinical setting, improvement in autonomic function as measured by spectral analysis is used as a surrogate marker for the suppression of the cytokine production. See, for example, the results of a spectral analysis set forth in Example 1 herein. The level of intracranial cytokines comes from sources within the central nervous system (e.g., classically activated microglia, imbalances cellular membrane omega-3: omega-6 fatty acid composition, toxic exposure, ischemia, hypoxia, inflammatory conditions, and infections) as well as from the periphery (e.g., chronic infections, bacterial translocation of LPS, autoimmune disorders, tobacco smoke inhalation, toxic exposures, vaccinations, chronic inflammatory conditions). It has been found that if cytokines are reduced substantially, neuronal progenitor stem cells increase in number and functionality, and the microglial populations shifts toward the M2-phenotype which repair neuronal damage and start producing anti-inflammatory cytokines (i.e., IL-4, IL-10, TNF-beta).

The consequence is the broad-based repair of damaged neurons throughout the brain, and is reflected in the recovery of autonomic function as noted on the sequential spectral analysis tests as well as reversal of patient's symptoms of dysautonomia (e.g., dizziness, fainting, urinary hesitation, urinary incontinence, urinary retention, dysfunction of erection or ejaculation, early satiety, loss of appetite, diarrhea, constipation, abdominal bloating, nausea, vomiting, difficulty swallowing, heartburn, excessive of deficient sweating, intolerance to light, poor vision at night, or exercise intolerance).

An additional consequence is the clinical improvement through the amelioration or alleviation of other chronic neuroinflammatory disorders such as chronic depression, post-traumatic stress disorder, epilepsy, autism spectral disorders, developmental delay, Alzheimer's disease, Parkinson's disease and chronic traumatic encephalitis. After the baseline test is performed as set forth in Example 1, the treatment regimen components provided herein are initiated and spectral analysis is repeated within a suitable timeframe, preferably approximately 2 months later, and the like (see FIG. 3). Once the spectral analysis is repeated and the relative change in the autonomic test results is assessed, additional steps can be taken to increase the potential inflammation suppression effect of the regimen, if improvement is not noted.

Methods for spectral analysis are well-known in the art and include the methods set forth in U.S. Pat. Nos. 7,079,888 and 7,529,579, incorporated herein by reference in their entirety.

As used herein, the term "antibiotic" refers to a naturally-occurring substance produced by a microorganism, such as, without limitation, a fungus or a yeast, the substance being useful in the treatment of infectious disease. Antibiotic also refers to semi-synthetic substances wherein a molecular version produced by a microorganism is subsequently modified to achieve desired properties. Preferred antibiotics for use herein include the well know class of compounds useful for reversing bacterial overgrowth in the intestinal track. Exemplary antibiotic for use herein include the antibiotic class including one or more of pyrimidine derivative, sulfonamide, quinolone, glycopeptides, beta-lactam, amphenicols, aminoglycoside and amino acid derivative. In yet other aspects, one or more antibiotics are selected from the group including one or more of rifaximin, chloramphenicol, penicillin G, vancomycin, carbenicillin, ciprofloxacin, mafenide, kanamycin, sisomicin, amikacin, trimethropin, D-cycloserine, gentamicin, dicloxacillin, nalidixic acid, thiamphenicol, levofloxacin, sulfamethizole and sulfisoxazole. In a preferred embodiment, the subject is treated with rifaximin at a dosage of 550 mg, 1 tablet by mouth 2-3 times daily for 10-14 days. This antibiotic treatment step is repeated as often as necessary based upon the suspicion of relapse of bacterial overgrowth.

In other embodiments, concomitant use of a second antibiotic such as metronidazole or neomycin may be required to adequately reverse small intestine bacterial overgrowth. In addition, because of the high rate of relapse that has been observed, treatment with antibiotics is preferably repeated every 12 months in all patients in order to reverse any low grade, subclinical bacterial overgrowth that may be recurring. It has been found that treatment with rifaximin with or without metronidazole or neomycin or any other antibiotic combination deemed necessary will reverse the excessive quantity of bacteria within the small intestine. The reduction of small intestinal bacterial load by using the antibiotics results in decreased pro-inflammatory cytokine production from translocation (i.e., leakage) of lipopolysaccharide (LPS) into the surrounding tissue. It has been found that leakage of LPS is a major element shown to result in the priming and activation of microglia within the brain. Microglia are generally in a resting or M2 phenotype, monitor neurons for signs of damage/distress, and actively engage in the repair of damaged neurons. Once activated (often referred to as priming) by substances such as LPS, the morphology and function of the M2-microglia changes significantly, and are often referred to as "primed", "classically activated" or M1-microglia.

Figure 1:
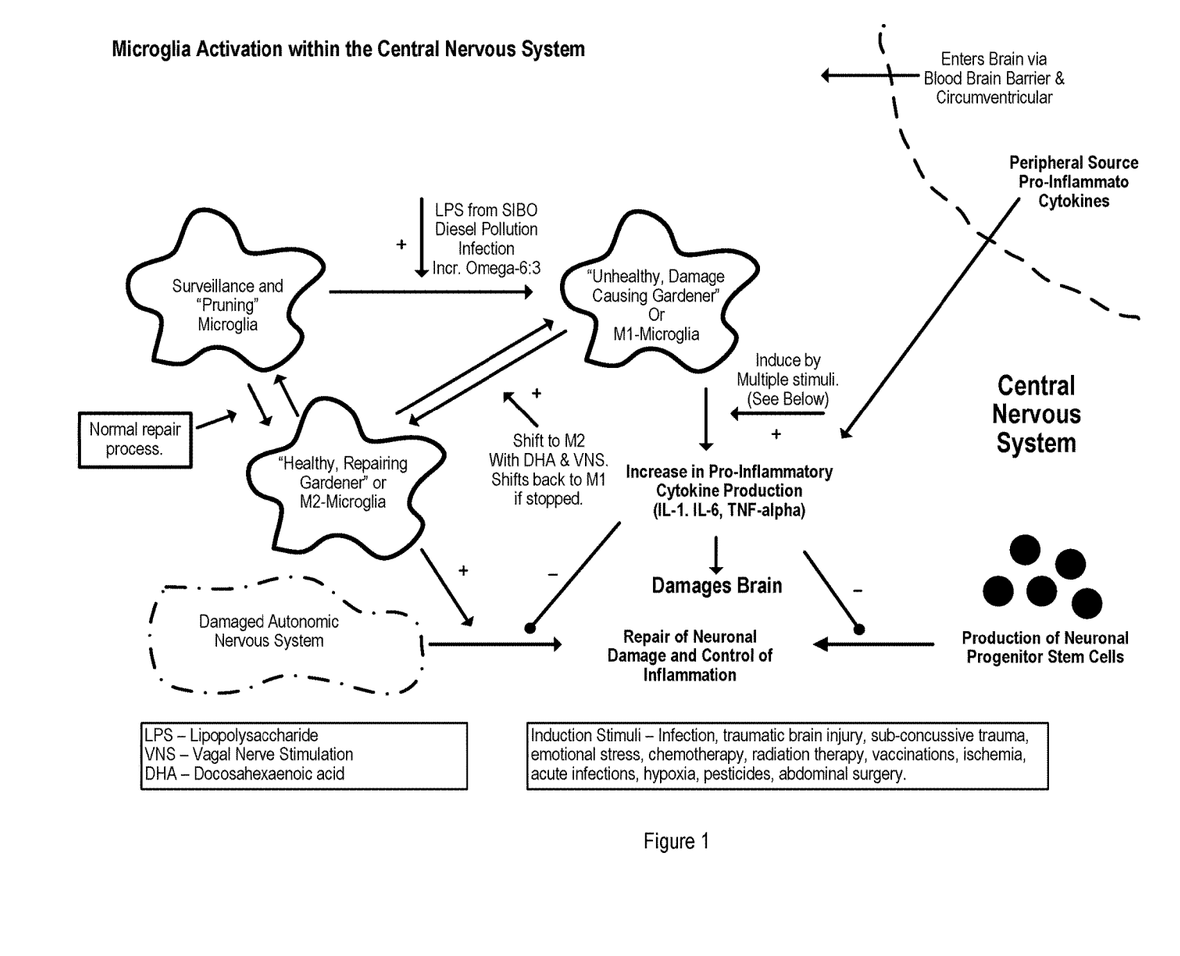
FIG. 1 shows a diagram of Microglia Activation within the Central Nervous System.
Figure 2:
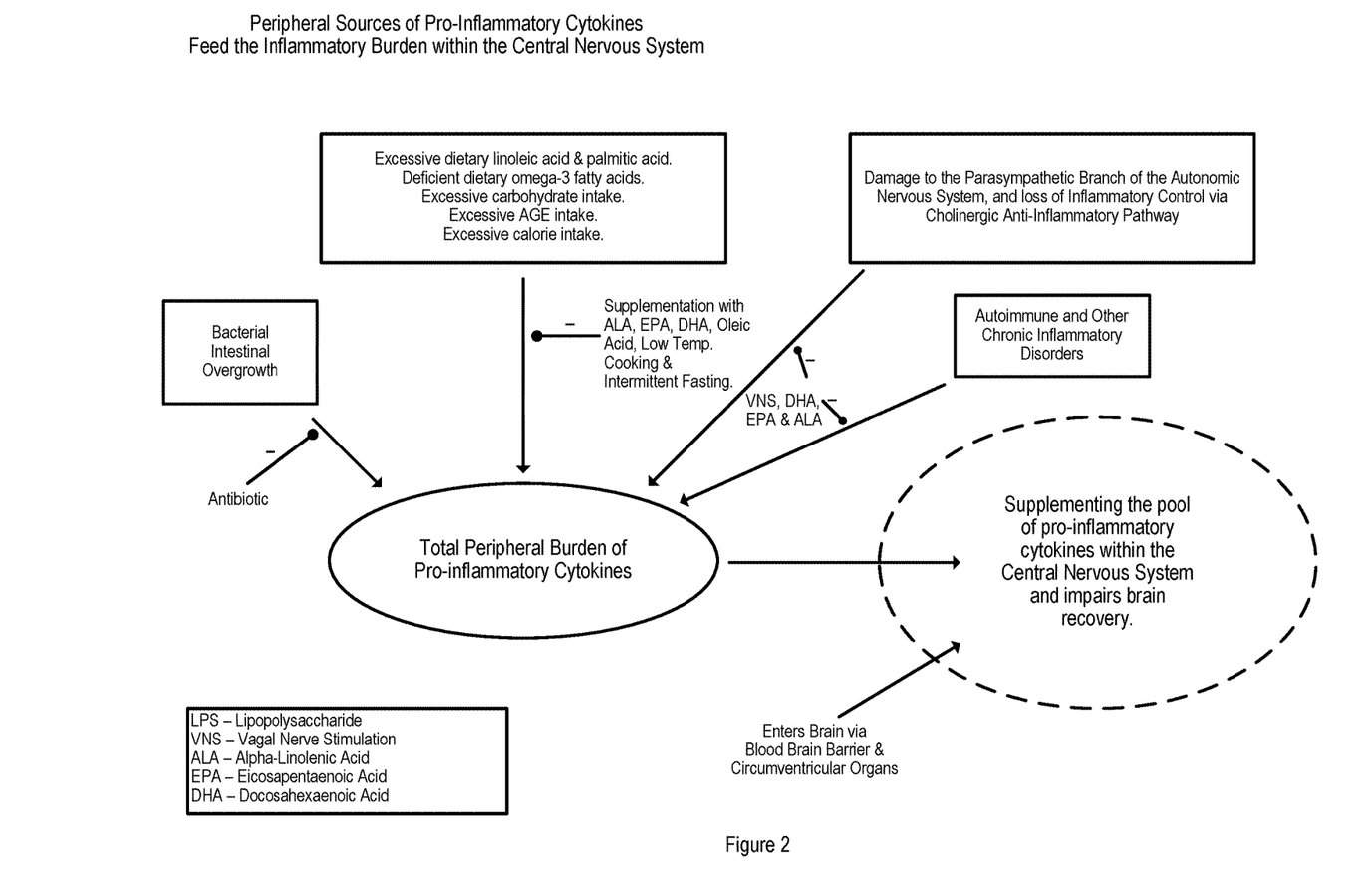
FIG. 2 shows a diagram depicting that Peripheral Sources of Pro-Inflammatory Cytokines Feed the Inflammatory Burden within the Central Nervous System.

M1-microglia produce excessive quantities of pro-inflammatory cytokines in response to brain injury, and contribute to progressive damage from neurodegenerative disorders (e.g., Alzheimer's disease, Parkinson's disease, chronic traumatic encephalopathy) or incomplete recovery from trauma (e.g., post-concussion syndrome, post-traumatic stress disorder, chronic depression). The excessive pro-inflammatory cytokine production of M1-microglia impair the ability of normal repair mechanisms (i.e., stem cell, astrocytes and M2-microglia) to repair damage to neurons and surrounding tissues. See FIGS. 1 and 2; and Table 1 of Luo, et al., Transl Neurodegener. 2012; 1:9, incorporated herein by reference in its entirety.

As used herein, the phrase docasahexaeonic acid or "DHA" refers to the well-known polyunsaturated omega-3 fatty acid. Fish oil contains 2 important polyunsaturated omega-3 fatty acids EPA (Eicosapentaenoic acid) and DHA, which can also be found in a variety of other dietary animal meats. Omega-3 fatty acids are often referred to as "essential" fatty acids because they are needed for human health but are not sufficiently produced by the body alone. EPA and DHA are naturally found in certain cold-water fatty fish such as salmon, tuna, and mackerel. They can also be derived in the body from alpha-linolenic acid (ALA), which is an omega-3 fatty acid found in certain seeds, plant-based oils, and animal-based oils.

The modern diet is typically deficient in omega-3 essential fatty acids and has become overloaded with pro-inflammatory omega-6 fatty acids, especially arachidonic acid. This heavy imbalance of omega-6 to omega-3 fatty acids in the modern diet is thought to lead to an overall inflammatory state that contributes to several diseases. The increased consumption of vegetable oils and shortenings, beef, and dairy is one of the major reasons for the high amount of omega-6 fatty acids in the diet and the imbalance between omega-6 to omega-3 fatty acids. The North American population, in particular, has among the lowest dietary intake of omega-3 fatty acids in the world and the highest intake of the pro-inflammatory omega-6 fatty acids.

For the invention methods provided herein, adequate amounts of omega-3 fatty acids, including EPA and DHA, are preferred and can be obtained in the diet from cold-water fatty fish such as salmon, tuna, and mackerel. It has been found that these omega-3 fatty acids are important precursors for a variety of inflammation-suppressing chemicals within the body. For example, DHA is the predominant omega-3 fatty acid within the nervous system, and has been found to be associated with reductions in the production of pro-inflammatory cytokines. Dietary sources of DHA are preferred, as they more readily penetrate and contribute to the needs of the central nervous system than are supplies of DHA converted from other dietary sources such as ALA or EPA, although these other dietary sources of DHA are also contemplated herein for use in the invention methods.

In preferred embodiments, DHA may be obtained from various sources, including natural sources and artificial sources. Natural sources include, without limitation, oils and fats from cold-water fish, such as shellfish, tuna, salmon, mackerel, herring, trout, and swordfish, anchovy, sardines, and possibly including certain types of algae. Fish are able to convert an omega-6 fatty acid, linolenic acid, in the algae to DHA to a reasonably fruitful degree whereas humans are only able to do so to a limited degree. Artificial sources include man-made DHA produced synthetically in the laboratory or by other suitable means, typically in the form of synthetic oils, waxes and fats, for inclusion into the present composition. Further non-limiting exemplary natural sources of DHA includes seed oil such as flaxseed oil, canola oil, vegetable oil, safflower oil, sunflower oil, nasturtium seed oil, mustard seed oil, olive oil, sesame oil, soybean oil, corn oil, peanut oil, cottonseed oil, rice bran oil, babassu nut oil, palm oil, low erucic rapeseed oil, palm kernel oil, among others.

It has also been found that DHA supplementation results in shifting the pro-inflammatory, neuron-damaging M1-microglia back to the anti-inflammatory, restorative M2-microglia. This results in the reduction of damage-promoting, and repair-inhibiting pro-inflammatory cytokines. In particular embodiments, high concentrations of DHA within the brain are employed to re-establish the function of natural repair mechanisms, and as a consequence, results in the reversal of underlying brain injury. In a particularly preferred embodiment, the source of DHA employed herein includes the high concentrations of DHA that can be found in liquid fish oils (e.g., in doses of 1-2 tablespoons per day depending on the brand and concentration), as well as in capsule form. See, e.g., U.S. Pat. No. 9,458,409, which is incorporated herein by reference in its entirety.

As used herein, "high concentrations of DHA" refers to DHA in the range of about 1,000-5,000 mg, more preferably about 2,000-4,000 mg of DHA. In a preferred embodiment of the invention methods, about 3,000 mg of DHA daily supplement is employed herein.

In another embodiment, daily dietary supplementation with ALA (alpha linolenic acid) containing foods or supplements is contemplated herein. As used herein the term "alpha-linolenic acid" refers to 9, 12, 15 octadecatrienoic acid, which has a short hand desimation of 18:3(n−3) and a molecular weight of 278.4. Throughout the specification alpha-linoienic acid is referred to as either alpha-linolenic acid or "ALA". This is a plant derived omega-3 fatty acid, which is commonly found in plants such as nuts, flax, hemp and chia. In accordance with a particular embodiment of the present invention, supplementation with approximately a ¼-½ cup of these food sources per day or 1000 mg of flax seed oil per day. Although ALA does not readily penetrate the brain, it has been found that supplementation reduces peripheral sources of pro-inflammatory cytokines which are capable of passing through the blood brain barrier, and worsening brain damage recovery. ALA has also been found to increases neurogenesis, synaptogenesis, and synaptic function in the rodent brain. It has also been found that ALA also increases tissue levels of DHA even in the brain.

As used herein, "oleic acid" refers to an omega-9 fatty acid that is typically present in olive oil, preferably extra virgin olive oil (EVOO). A suitable amount of oleic acid for use herein contains enough oleic acid necessary to reduce tissue concentrations of linoleic acid and arachidonic acid, which are omega-6 fatty acids involved in the production of pro-inflammatory mediators. In a preferred embodiment, a daily supplement of a suitable amount of extra virgin olive oil is consumed. In some embodiments, the range of EVOO is from about 5 ml to about 100 ml, about 10 ml to about 75 ml, about 15 ml to about 50 ml, about 20 ml to about 40 ml, with about 25 ml daily of EVOO being particularly preferred. It has been found that the reduced levels of pro-inflammatory mediators within the brain have been linked to the reversal of neuronal damage. It is also believed that the phenolic compounds contained within extra virgin olive oil have a variety of other anti-inflammatory and health promoting effects including improvements in cellular function, oxidation, reduced microbial activity, and a reduction in the level of pro-inflammation mediators.

Figure 5:
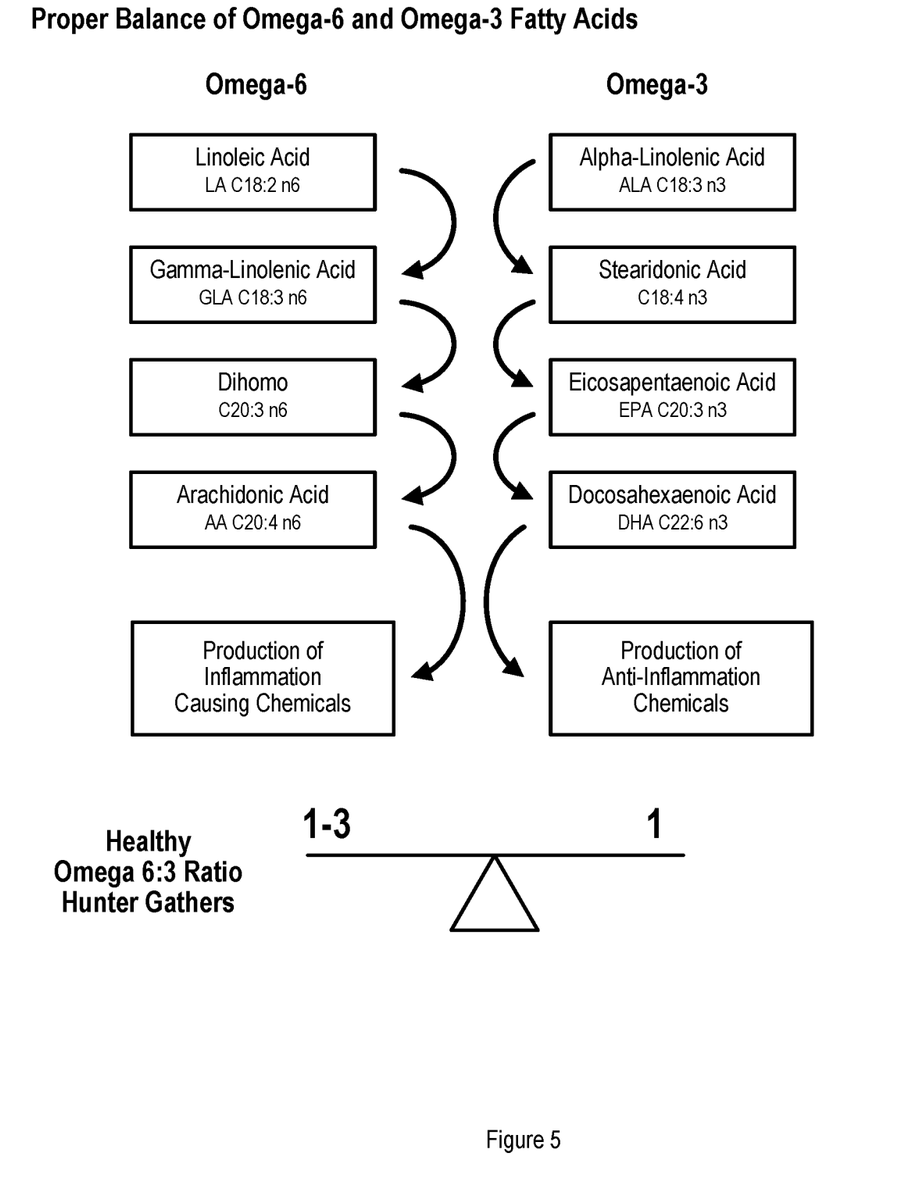
FIG. 5 shows the Proper Balance of Omega-6 and Omega-3 Fatty Acids.

In the methods utilized herein, it is preferable to restrict the consumption of cooking oils containing high ratios of omega-6 to omega-3 fatty acids. For example, it has been found that a healthy balance of cellular omega-6 and omega-3 fatty acids is required to maintain inflammation homeostasis within the brain and body. Consequently, preferred cellular and dietary fatty acid ratios of omega-6 to omega-3 fatty acids are in the 1-3 to 1 range (e.g., within 1-3:1 omega-6:omega-3; see FIG. 5).

It has also been found that restriction of inflammation-promoting omega-6 fatty acids, linoleic acid and arachidonic acidomega-6 fatty has the combined effect of reducing the production of inflammation-promoting mediators; and also has the consequence of increasing levels of DHA within the brain. Dietary linoleic acid is most commonly consumed in the form of plant oils such as soy oil, corn oil, safflower oil, sunflower oil, vegetable oil, grapeseed oil, margarine and shortenings. These oils are to be preferably avoided and are commonly consumed as an ingredient in prepared commercial foods.

In the methods utilized herein it is preferred to consume cooking oils containing evenly balanced ratios of omega-6 to omega-3 fatty acids. As set forth above, preferred cellular and dietary fatty acid ratios are in the 1-1 to 3-1 (omega-6:omega-3) range. Exemplary oils having the desired 1-to-1 omega-3:omega-6 ratios, include for example, canola, butter, palm kernel oil, and the like. It has been found that the reduction in dietary omega-6 acid intake increases bioavailability of omega-3 polyunsaturated fatty acids in the bloodstream. Accordingly, switching prepared food items to those with 1-to-1 ratios is highly preferable to reduce inflammation within the brain.

As used herein, the phrase "vagus nerve stimulation" or "VNS" refers to the stimulation of the auricular branch of the vagus nerve. The vagus nerve can be stimulated using methods well known in the art, including internally via a transplanted device (e.g., U.S. Pat. No. 9,211,410; incorporate herein by reference in its entirety), mechanically, or transcutaneously. Transcutaneous vagus nerve stimulation (tVNS) of the auricular branch of the Vagus nerve (FIG. 6) results in the reduction of pro-inflammatory cytokines via the cholinergic anti-inflammatory pathway (Lerman et al., Neuromodulation 19:283-291, 2016; incorporated herein by reference in its entirety). As used herein, the term "vagus nerve" is used in its broadest sense, and includes any nerves that branch off from the main vagus nerve, as well as ganglions or postganglionic neurons that are connected to the vagus nerve. The vagus nerve is also known in the art as the parasympathetic nervous system and its branches, and the cholinergic nerve.

In certain embodiments, the vagus nerve can be stimulated by any means known to those of skill in the art. Nonlimiting examples include: mechanical means such as a needle, ultrasound, or vibration. Mechanical stimulation can also be carried out by carotid massage, oculocardiac reflex, dive reflex and valsalva maneuver. The efferent vagal nerve fibers can also be stimulated by electromagnetic radiation such as infrared, visible or ultraviolet light; heat, or any other energy source. The efferent vagus nerve can be stimulated by stimulating the entire vagus nerve (i.e., both the afferent and efferent nerves), or by isolating efferent nerves and stimulating them directly. The latter method can be accomplished by separating the afferent from the efferent fibers in an area of the nerve where both types of fibers are present. Alternatively, the efferent fiber is stimulated where no afferent fibers are present, for example close to the target organ served by the efferent fibers.

The efferent vagus nerve fibers can also be stimulated by stimulating the target organ directly, e.g., electrically, thus stimulating the efferent fibers that serve that organ. In other embodiments, the ganglion or postganglionic neurons of the vagus nerve can be stimulated. In preferred embodiments set forth herein, the vagus nerve is stimulated electrically, using any electrical means known to those of skill in the art. For example, commercial vagus nerve stimulators for use herein include the Cyberonics NCP®, the NEMOS® device for t-VNS, or a transcutaneous electrical nerve stimulation (TENS) unit, such as the TENS 7000 (Roscoe Medical, Strongsville, Ohio), and the like.

In combination with the methods provided herein, the amount of stimulation useful to inhibit inflammatory cytokines, such as in an inflammatory cytokine cascade, can be determined by the skilled artisan without undue experimentation for any condition to be treated. In one embodiment, to inhibit a systemic inflammatory cytokine cascade, a constant voltage stimuli of about 1 to 5 V, at 2 ms and 1 Hz, for 10 minutes is contemplated herein to inhibit the systemic inflammatory cytokines sufficiently.

In certain embodiments, the electrical stimulation is achieved by clipping electrodes across the tragus of the ear, inducing an electrical current with a TENS (transcutaneous electrical nerve stimulation) unit with the frequency in the range selected from about 0.1 Hz to about 30 Hz, about 0.3 Hz to about 25 Hz, about 0.5 Hz to about 20 Hz, about 0.7 Hz to about 15 Hz, about 0.9 Hz to about 10 Hz, about 1.0 Hz to about 9 Hz, about 1.2 Hz to about 8 Hz, about 1.4 Hz to about 7 Hz, about 1.6 Hz to about 6 Hz, or about 2 Hz to about 5 Hz. In these embodiments the pulse width can be in the range selected from about 20 to about 1000 uS, about 30 to about 900 uS, about 40 to about 800 uS, about 50 to about 700 uS, about 60 to about 600 uS, about 70 to about 500 uS, about 80 to about 450 uS, about 90 to about 400 uS, about 100 to about 350 uS, about 110 to about 325 uS, about 120 to about 300 uS, about 130 to about 275 uS, about 140 to about 260 uS, or about 150 to about 250 uS. In these embodiments, the current can be in a range selected from about 0.1 to about 5.0, about 0.2 to about 4.0, about 0.3 to about 3.0, about 0.4 to about 2.0, or about 0.5 to about 1.0 mAmps (see FIG. 6). In a particularly preferred embodiment, the electrical stimulation is achieved by inducing an electrical current with a TENS (transcutaneous electrical nerve stimulation) unit with the frequency at 2-5 Hz, pulse width at 150-250 uS and 0.5-1.0 mAmps (see FIG. 6). It is contemplated herein, that the tVNS is employed for an amount of time sufficient to adequately reduce the pro-inflammatory cytokines via the cholinergic anti-inflammatory pathway. Suitable times for use herein include about 30 minutes up to about 8 hours per day, more preferably 45 minutes up to about 7 hours, more preferably 1 hour up to about 6 hours, more preferably 1.5 hours up to about 5 hours, with about 2 hours up to about 4 hours per day being particularly preferred.

Over-nutrition refers to the toxic cellular effects excessive nutrients inflict on the body. The voluntary or involuntary (i.e., increased levels of hunger from autonomic dysfunction or intestinal bacterial overgrowth) of excess calories will initially result in the growth of adipose tissue. As long as the excessive calories can be stored within subcutaneous adipose tissue, they are for the most part harmless to metabolic function and overall heath. However, for a variety of reasons known and unknown, many individuals reach a point where they are unable to store calories within adipose. The excessively ingested calories then flow within cells of the brain and other organs, and the cells begin to function abnormally. These cells are being damaged due to over-nutrition from excessive caloric intake.

The endoplasmic reticulum (referred to as ER; an internal organelle responsible for the production of proteins and lipids) is the portion of the cell most adversely affected by over-nutrition. Endoplasmic reticular stress (ER stress) is a common component of the major neurodegenerative disorders (Alzheimer's Disease, Parkinson's Disease, Amyotrophic Lateral Sclerosis, Lewy Body Dementia, Age-Related Macular Degeneration), and is responsible for the pathological development of inclusion bodies. ER stress from overnutrition impairs autophagy (the ability of brain cells to remove damaged or unneeded proteins and lipids collecting within the cells). The build-up of intracellular proteins within the cell in the intracytoplasmic inclusion bodies (e.g., tau, alpha-synuclein, Lewy Bodies) which are common features in neurodegenerative disorders.

The use of intermittent fasting in the Nemechek Protocol invention methods provided herein creates a health-promoting level of cellular stress that causes cells to repair themselves and restore function. This positive stress is known as hormesis, and it can restore normal cell function, reduce levels of pro-inflammatory cytokines, and repair damaged cells within the brain as well as in peripheral organs. Importantly, hormesis will increase autophagy. Autophagy is the key feature required to reverse the build-up of intracytoplasmic inclusion bodies that is a central pathological component of the neurodegenerative disorders.

For example, the neurological benefits of using the Intermittent Fasting step in the Nemechek Protocol invention methods provided herein, include: improved Autophagy; improved Mitochondrial Function; reduced LPS-Induced Neuroinflammation; neuroprotection following Traumatic Brain Injury; improved Endoplasmic Reticular Function; increased Brain Stem Cell Production; increases Resistance to Brain Damage; improvement in Cognitive Functioning; and reversing cellular changes of Alzheimer's Disease and of Parkinson's Disease.

As used herein, the phrase "placing said subject on an intermittent fasting regimen" refers to requiring and/or scheduling the subject for the significant reduction of caloric intake, preferably at least once weekly (e.g., one fasting-day per week); to up to 3 non-consecutive fasting-days per week. In certain embodiments contemplated herein, on a "fasting-day" as referred to herein, total dietary caloric intake is reduced to less than 1000, less than 900, less than 800, less than 700, less than 600 or less than 500 calories per fasting-day for women and less than 1200, less than 1100, less than 1000, less than 900, less than 800, less than 700, or less than 600 calories per fasting-day for men. In a particularly preferred embodiment, total dietary caloric intake is reduced to less than 500 calories per fasting-day for women and less than 600 calories per fasting-day for men.

In certain embodiments, the intermittent fasting regimen may be initiated at the baseline visit, when the administration of the antibiotic, polyunsaturated omega-3 fatty acid, oleic acid and the vagus nerve stimulation are initiated, if the patient does not exhibit any symptoms suggestive of cerebral hypoperfusion such as orthostasis, occipital headaches or neck tightness. If these symptoms are present, it is preferable to wait until the 2nd or 3rd clinical visit to initiate the intermittent fasting regimen otherwise the patient may experience increases in hunger, anxiety, headaches and orthostasis.

Figure 4:
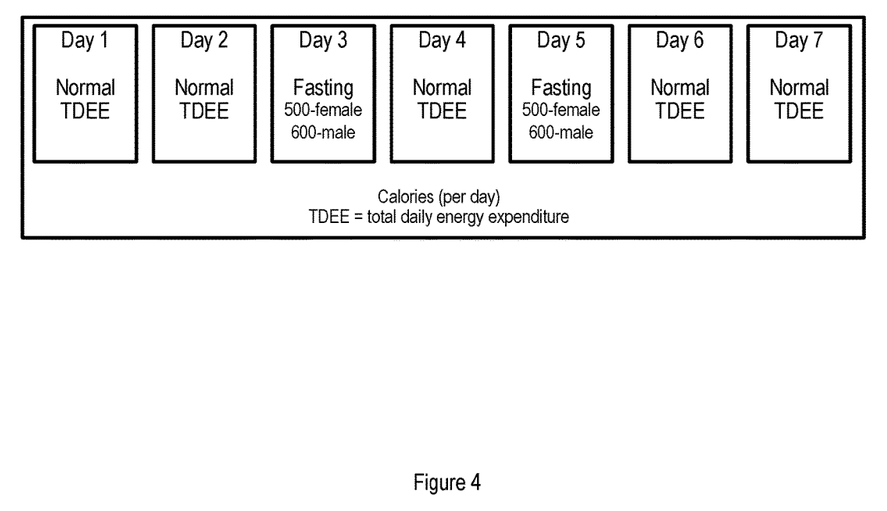
FIG. 4 shows the depiction of a 5:2 Intermittent Fasting Regimen.

In another embodiment, the basic format of intermittent fasting regimen is to alternate days of 'normal' calorie consumption with fasting-days when calorie consumption is severely restricted. This can either be done on an alternating day basis as set forth herein, or using the well-known 5:2 strategy in which 2 days each week are classed as fasting-days (see FIG. 4). It has been found that the excessive consumption of calories results in a form of cellular stress known as endoplasmic reticular stress, and also results in increases in pro-inflammatory cytokines within the central nervous system as well as peripheral tissues. It has also been found that intermittent fasting regimens limit neuronal damage and improve recovery after stroke, Parkinson's disease and Huntington's disease; and also attenuate pro-inflammatory cytokine production in response to LPS exposure from intestinal bacterial overgrowth.

Many patients with autonomic damage are unable to regulate the proper amount of arterial blood flow and oxygen delivery to the brain. Cerebral hypoperfusion is the primary cause of symptoms (i.e., headaches, neck tightness, anxiety, lightheaded/dizziness, decreased cognitive function) in a concussed individual. Patients with cerebral hypoperfusion often experience an increased level of hunger and thirst because the subconscious mind sense learns that by increasing the intake of liquids or foods with contain salt and sugar, cerebral perfusion and oxygen delivery is temporarily improved.

The significant decline of calories required by intermittent fasting (e.g, the total intake of only 500-600 calories, and the like) reverses the beneficial effect of food and drink on cerebral perfusion. As set forth herein, the use of the intermittent fasting step is contemplated in the invention methods at the onset of the Nemechek Protocol invention methods provided herein. However, if intermittent fasting is initiated at the onset of the Nemechek Protocol, it can result in the worsening of symptoms (headaches, fatigue, anxiety, poor concentration, altered balance and lightheadedness). Accordingly, in a preferred embodiment for use with the invention methods, intermittent fasting is not implemented in a range selected from until about 0-12 months, about 1-10 months, about 2-8 months, about 3-6 months, or about 3-4 months, after initiation of administering the antibiotic, polyunsaturated omega-3 fatty acid, and oleic acid with or without vagal nerve stimulation, when symptomatic improvement of cerebral hypoperfusion has been achieved. In a particularly preferred embodiment for use with the invention methods, intermittent fasting is not implemented until about 3-4 months after initiation of administering the antibiotic, polyunsaturated omega-3 fatty acid, and oleic acid with or without vagal nerve stimulation, when symptomatic improvement of cerebral hypoperfusion has been achieved.

In some embodiments, daily supplementation with curcumin is optionally employed in the methods described herein. In particular embodiments, curcumin supplementation can occur either once or twice daily. The amount of curcumin taken daily can range from about 100 mg up to about 5000 mg, about 200 mg up to about 4500 mg, about 300 mg up to about 4000 mg, about 400 mg up to about 3500 mg, about 400 mg up to about 3000 mg, about 500 mg up to about 2500 mg, about 600 mg up to about 2000 mg, about 700 mg up to about 2000 mg, about 800 mg up to about 1500 mg, with about 1000 mg taken twice daily being especially preferred.

Curcumin is derived from the spice turmeric, and is a potent anti-inflammatory agent that is added to the initial regimen if an individual is believed to have a significant inflammatory component from a comorbid autoimmune disorder. In one embodiment, curcumin may be added to any patient's regimen if there is inadequate clinical or autonomic improvement after about 2 months of treatment without the use of curcumin.

Any form of curcumin known to those of skill in the art can be utilized herein. For example, curcumin in the form of colloidal, nanoparticles, oil emersions or special blends are contemplated herein for use in reducing inflammation. Nearly 80% of the cells of immune system are located within the tissues immediately surrounding the lumen of the small intestine often referred to as Peyer's patches. It has been found that curcumin is able to readily saturate this area without entering the blood stream, and in doing so comes in contact with a large proportion of the immune system and results in the reduction in the production of pro-inflammatory cytokines.

In another embodiment of the methods herein, the reduction of total dietary carbohydrate intake to less than about 40-100 grams per day is optionally employed. It has been found that reduction in dietary carbohydrates to less than 100 grams per day decreases hunger and total caloric intake as well as the level of pro-inflammatory cytokines production. In addition to a reduction in hunger, it has also been found that reducing caloric intake and dietary carbohydrates to less than 40 grams per day increases ketone production making this alternative cellular fuel available for neurons, while providing additional protection from injury.

In other embodiments of the methods set forth herein for individuals intolerant to omega-3 intake from fish or individuals who choose not consume fish-derived products (e.g., vegetarians), individuals can optionally consume other oils or foods that have high concentrations of alpha-linolenic acid (ALA). Exemplary foods having high ALA concentrations include, for example, flax oil, chia, kiwifruit seeds, *perilla*, lingonberry, purslane, sea buckthorn, and the like. In a particular embodiment, supplementation with 3,000 mg of flax seed oil twice daily is contemplated herein. It has been found that high concentrations of alpha-linolenic acid can increase the production of DHA and increase accretion of DHA within the brain.

The treatment of any condition mediated by the suppression of pro-inflammatory cytokines is within the scope of the invention methods provided herein. As used herein, the phrase "suppression of pro-inflammatory cytokines" refers to the combined effect of the invention treatment methods to substantially reduce the levels of pro-inflammatory cytokines within the central nervous system such that natural repair mechanisms are activated and autonomic nervous system function recovers. As set forth herein, autonomic recovery is detected by sequential spectral analysis monitoring of the autonomic nervous system. If no recovery is noted, the treatment regimen can be supplemented further.

In preferred embodiments, the diseases or conditions treated herein by the suppression of pro-inflammatory cytokines are traumatic brain injury, concussion, chronic traumatic encephalopathy (CTE), post-concussion syndrome (PCS), Alzheimer's disease, Parkinson's disease, autism, essential tremor, post-traumatic stress disorder (PTSD), chronic depression, treatment resistant epilepsy, autism, developmental delay and sensory perception disorder.

The disease or condition can be one where the pro-inflammatory cytokines cause a systemic reaction. Alternatively, the condition can be mediated by a localized pro-inflammatory cytokines, such as in rheumatoid arthritis, and the like. Additional non-limiting examples of inflammatory disorders or diseases which can be treated using the present invention include appendicitis, peptic, gastric or duodenal ulcers, peritonitis, pancreatitis, ulcerative, pseudomembranous, acute or ischemic colitis, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopicsilicovolcanoconiosis-, alvealitis, bronchiolitis, pharyngitis, pleurisy, sinusitis, influenza, respiratory syncytial virus, herpes, disseminated bacteremia, Dengue fever, candidiasis, malaria, filariasis, amebiasis, hydatid cysts, burns, dermatitis, dermatomyositis, sunburn, urticaria, warts, wheals, vasculitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillain-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Bechet's syndrome, allograft rejection, graft-versus-host disease, Type I diabetes, ankylosing spondylitis, Berger's disease, Reiter's syndrome, or Hodgkin's disease. In more preferred embodiments, the condition is appendicitis, peptic, gastric or duodenal ulcers, peritonitis, pancreatitis, ulcerative, pseudomembranous, acute or ischemic colitis, hepatitis, Crohn's disease, asthma, allergy, anaphylactic shock, organ ischemia, reperfusion injury, organ necrosis, hay fever, sepsis, septicemia, endotoxic shock, cachexia, septic abortion, disseminated bacteremia, burns, Alzheimer's disease, coeliac disease, congestive heart failure, adult respiratory distress syndrome, cerebral infarction, cerebral embolism, spinal cord injury, paralysis, allograft rejection or graft-versus-host disease.

Other diseases contemplated herein for treatment using the invention methods provided herein include hay fever, atherosclerosis, arthritis (rheumatoid, bursitis, gouty arthritis, polymyalgia rheumatic, etc.), asthma, autoimmune diseases, chronic inflammation, chronic prostatitis, glomerulonephritis, nephritis, inflammatory bowel diseases, pelvic inflammatory disease, reperfusion injury, transplant rejection, vasculitis, myocarditis, colitis, and the like.

Also provided herein, are methods for preventing, reducing or reversing acute and/or chronic autonomic damage by suppression of pro-inflammatory cytokines in a subject in need thereof, comprising administering to said subject an effective amount of an antibiotic; an effective amount of polyunsaturated omega-3 fatty acid; and an effective amount of oleic acid; and providing VNS (vagal nerve stimulation) to the subject.

EXAMPLES

Example 1—Spectral Analysis of Normal Baseline Subjects And Subjects Treated with Various Combinations of Antibiotic, DHA Supplement, Oleic Acid and Vagal Nerve Stimulation Therapy A. Spectral Analysis:

Prior to initiating the Nemechek Protocol employing the invention methods, autonomic monitoring is performed on each prospective patient via a baseline spectral analysis using the ANX Version 3.0 Autonomic Nervous System Monitor, available from ANSAR Medical Technologies Inc. (Philadelphia Pa.).

Briefly, as described in the ANX monitor protocol, the first step is to seat patient in a comfortable chair with sufficient back support. The chair should be stationary and not swivel, tilt, rock, or have wheels/casters. Next, place the Blood Pressure (BP) cuff on patient's upper left arm. Follow the instructions on the cuff to insure proper placement. Note that you may manually start and stop the BP monitor by clicking on the NIBP Start/Stop toggle switch on the front of the data acquisition screen. Next, the white and black leads are placed on patient's upper chest just below the clavicle, each approximately 1.5-2 inches out from the sternum. The white lead is placed on the right, the black on the left. The red lead is placed at the base of patient's rib cage on patient's left. As a final step, instruct the patient that throughout the test she/he should remain as still as possible with feet flat on the floor, not talk, and simply breathe freely at a comfortable pace unless instructed to do otherwise (e.g., during the Deep Breathing and Valsalva challenges).

Testing Phases:

| | | |
|---|---|---|
| Baseline | Instruct patient to breathe at a relaxed, normal pace. | 5 minutes |
| Deep Breathing | Instruct patient to breathe 5 seconds in, 5 seconds out, and to breathe at a slow and easy pace. This should be done correctly to accurately challenge the parasympathetic nervous system. | 1 minute |
| Baseline | Instruct patient to breathe at a relaxed, normal pace. | 1 minute |
| Valsalva | Patient should perform the first Valsalva with a 15-second hold, then relax until the clock reads 1:00. Patient should then do 4 Valsalva's, one every 15 seconds. Instruct patient to take a quick breath in and hold it. Then, like inflating a hard balloon, tell patient to create pressure in her/his chest, pushing out and down on the stomach while holding and bearing down on the breath. (This feeling is also compared with straining while having a bowel movement.) Bearing down on the breath is the single most important part of this challenge. Discontinue Valsalva if patient feels chest pain. | 95 seconds |
| Baseline | Instruct patient to breathe at a relaxed, normal pace. | 2 minutes |
| Stand | Instruct patient to stand as quickly as possible. Patients requiring assistance may be helped without compromising the test. Watch carefully for signs of dizziness or loss of balance. | 5 minutes |

NOTE:

If a patient is not able to perform the Stand challenge (for whatever reason), the test should be performed in a supine position for the first five (5) phases. However, at the Stand portion of the test, the patient should be instructed to sit up from the supine position. The patient may be assisted in doing so, if necessary.

B. Nemechek Protocol Treatment:

Briefly, there was a Control Group (Normal) and 3 Groups of patients who were treated with either: antibiotic and DHA supplement (referred to herein as the "SD" group; 116 patients); antibiotic, DHA supplement and oleic acid (referred to herein as the "SDE" group' 212 patients); or antibiotic, DHA supplement, oleic acid, and vagal nerve stimulation (referred to herein as the "SDEV" group; 77 patients). The results of these treatments are provided below.

More specifically, to the patients of the SD group, 550 mg of the antibiotic rifaximin was administered 2-3 times daily for 10-14 days. To this same SD patient group, 3,000 mg of DHA supplement was administered daily.

To the SDE patient group, in addition to antibiotic and DHA supplement administered as above with the SD group, oleic acid in the form of extra virgin olive oil was administered by giving the SDE patients 25 ml of extra virgin olive oil (EVOO) per day.

Figure 6:
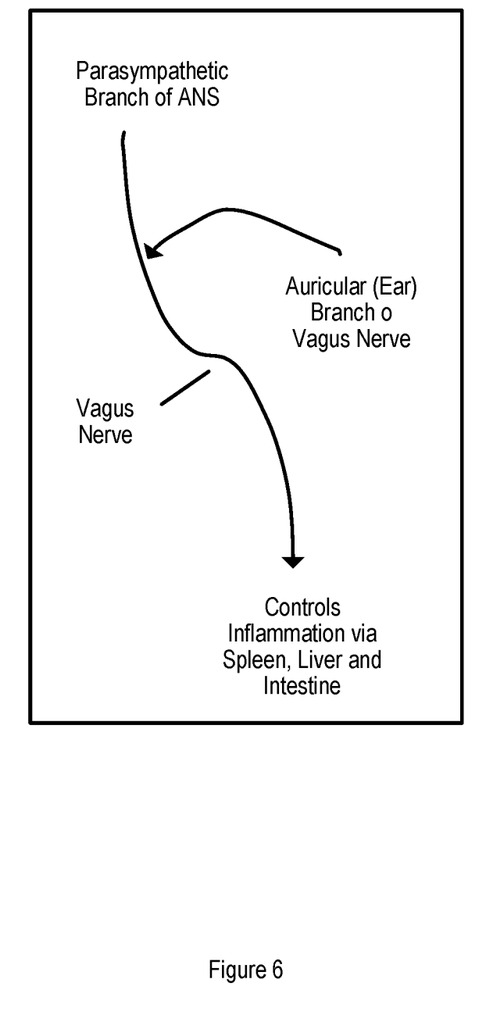
FIG. 6 shows the Transcutaneous vagus nerve stimulation (tVNS) of the Auricular Branch of the Vagus Nerve; and depicts that electrical stimulation of the auricular branch of the Vagus nerve at the tragus will trigger an anti-inflammatory response via the spleen, liver and intestinal tract.

For the SDEV patient group, in addition to being administered antibiotic, DHA supplement and oleic acid in the form of EVOO, the SDEV group was subjected to electrical vagal nerve stimulation by clipping electrodes across the tragus of the left ear, inducing an electrical current with a TENS (transcutaneous electrical nerve stimulation) 7000 unit (available from Roscoe Medical, Strongsville, Ohio), with the frequency at 2-5 Hz, pulse width at 150-250 uS and 0.5-1.0 mAmps (see FIG. 6).

TABLE 1

Population Averages

| | N | % F | Age (yrs) | BMI (#/in$^2$) |
|---|---|---|---|---|
| Normal | 334 | 52 | 46 | 25.9 |
| SD | 116 | 60 | 46 | 29.0 |
| SDE | 212 | 50 | 68 | 29.0 |
| SDEV | 77 | 53 | 64 | 34.4 |

TABLE 2

Data independence:

| P | SD vs SDE | SD vs SDEV | SDE vs SDEV | SD vs Nml | SDE vs Nml | SDEV vs Nml |
|---|---|---|---|---|---|---|
| Bx LFa | 0.04 | −0.02 | 0.00 | 0.02 | 0.05 | 0.02 |
| Bx RFa | 0.05 | −0.04 | 0.05 | 0.03 | −0.01 | 0.01 |

When comparing the three patient groups' Sympathetic (LFa) and Parasympathetic (RFa) responses, all three groups are found to be independent (statistically, significantly different: $p \leq 0.05$, see Table above). When comparing the three patient groups with a normal subject population, at the baseline study, all groups are statistically, significantly different ($p \leq 0.05$).

TABLE 3

Resting Baseline Statistical Means Baseline (Test 1) Responses compared with normal subjects:

|  | Bx LFa | Bx RFa | SB | DB RFa | V LFa | V, PE (%) | PC LFa | PC, PE (%) |
|---|---|---|---|---|---|---|---|---|
| Normal | 3.27 | 3.55 | 1.30 | 42.00 | 53.10 | 0.00 | 5.20 | 0.00 |
| SD | 3.81 | 2.83 | 2.10 | 34.43 | 61.29 | 90.18 | 7.06 | 61.61 |
| SDE | 2.46 | 2.40 | 1.99 | 32.59 | 54.89 | 89.81 | 5.33 | 68.93 |
| SDEV | 2.06 | 1.90 | 2.24 | 25.57 | 43.93 | 92.86 | 21.28 | 71.43 |

NOTE:
1) SB is the average of ratios, not the ratio of averages, therefore it is not always equal to the simple ratio of the average Bx LFa to Bx RFa.
Abbreviations:
LFa—Sympathetic Response,
RFa—Parasympathetic Response Bx—Baseline,
DB—Deep Breathing,
V—Valsalva,
PE—Parasympathetic Excess,
PC—Postural Challenge.

Dynamic Parasympathetic Excess (PE) in response to both Valsalva (V, PE) and stand (postural change, or PC, PE) are prevalent in all patient populations at baseline testing. PE (whether Valsalva or stand) is associated with the following: difficult to control BP, blood glucose, or hormone level, difficult to describe pain syndromes (including CRPS), difficult to manage weight-loss, unexplained arrhythmia (palpitations) or seizure, and symptoms of depression or anxiety, fatigue, exercise intolerance, sex dysfunction, sleep or GI disturbance, lightheadedness, or frequent headache or migraine. PE with stand may also mask Sympathetic Withdrawal (SW) which underlies Orthostatic Dysfunction. Regarding therapy, Valsalva Sympathetic Excess is considered secondary to Valsalva PE.

Low HRV is associated with low Parasympathetic (P) activity, which is associated with increased levels of pro-inflammatory cytokine, which is associated with impairment of the vagal-mediated acetylcholine inflammatory reflex. Total Spectral Power (TSP) is a measure of HRV. TSP is the sum of LFa+RFa. As compared with normal subjects, (LFa+RFa=6.82 $bpm^2$), the average HRV (or TSP) response for the three study populations are all lower as compared with normal: SD, TSP=6.64 $bpm^2$ (p=0.02); SDE, TSP=2.86 $bpm^2$ (p=0.01); SDEV, TSP=3.96 $bpm^2$ (p=0.01).

Pre-existing low HRV, from an inflammatory perspective, correlates with the risk of developing PTSD. The prevalence of PTSD was higher in subjects with high pre-incidence LFa/RFa ratios (SB). The normal range for SB is modified by age. Patients younger than 65 years normally have a higher normal SB: 1.0<SB<3.0; otherwise they tend to be depressed. Older patients are recommended to normally have a lower normal SB: 0.4<SB<1.0; to afford a "little more" parasympathetic activity as cardio-protective [Singer, JACC, 1998]. Based on these ranges and the average ages of the study populations, the SDE & SDEV populations demonstrate high pre-incident SB and the SD populations demonstrate normal (p<0.05).

After anti-biotic and DHA supplement (SD) therapy, there was no significant change in the average resting, Sympathetic (Bx LFa) responses ($\Delta$=0.02 $bpm^2$, p=0.56) or Sympathovagal Balance (SB) responses ($\Delta$=−0.01 $bpm^2$, p=0.36), while the average, resting Parasympathetic (Bx RFa) increased by 45.6% ($\Delta$=1.29 $bpm^2$, p=0.03). The changes in the dynamic responses to SD therapy included insignificant decreases in deep breathing Parasympathetic activity (DB RFa: $\Delta$=−1.77 $bpm^2$, p=0.83), Valsalva Sympathetic activity (V LFa: $\Delta$=−9.79 $bpm^2$, p=0.44), and stand Sympathetic activity (PC LFa: $\Delta$=−0.61 $bpm^2$, p=0.67). However, the prevalence of the abnormal, dynamic PEs both decreased significantly: V, PE decreased by 40.2% (p=0.04) and PC, PE decreased by 21.4% (p=0.01).

After adding oleic acid with SD therapy (SDE therapy), there was no significant change in the average resting, Sympathetic responses ($\Delta$=−0.43 $bpm^2$, p=0.57) or Sympathovagal Balance (SB) responses ($\Delta$=−0.02 $bpm^2$, p=0.37). The average, resting Parasympathetic response increased, but not significantly ($\Delta$=0.30 $bpm^2$, p=0.14). The changes in the dynamic responses to SDE therapy included an insignificant increase in deep breathing Parasympathetic activity ($\Delta$=6.42 $bpm^2$, p=0.99), an insignificant decrease in Valsalva Sympathetic activity ($\Delta$=−11.13 $bpm^2$, p=0.81), and an insignificant increase in stand Sympathetic activity ($\Delta$=1.36 $bpm^2$, p=0.79). However, the prevalence of the abnormal, dynamic PEs both decreased significantly: V, PE decreased by 24.3% (p=0.04) and PC, PE decreased by 16.5% (p=0.02).

After adding Vagal N. stimulation with SDE therapy (SDEV therapy), there were significant changes in the average resting, Sympathetic responses ($\Delta$=2.34 $bpm^2$, p=0.01) and average, resting Parasympathetic responses ($\Delta$=1.34 $bpm^2$, p=0.05). Sympathovagal Balance (SB) responses also increased, but not significantly ($\Delta$=0.95 $bpm^2$, p=0.33). The changes in the dynamic responses to SDEV therapy included an insignificant decrease in deep breathing Parasympathetic activity ($\Delta$=−2.01 $bpm^2$, p=0.87), an insignificant decrease in Valsalva Sympathetic activity ($\Delta$=−2.12 $bpm^2$, p=0.76), and an insignificant decrease in stand Sympathetic activity ($\Delta$=−0.26 $bpm^2$, p=0.63). However, the prevalence of the abnormal, dynamic PEs both decreased significantly: V, PE decreased by 48.6% (p=0.01) and PC, PE decreased by 32.9% (p=0.01).

In summary and on average among the three therapy modalities, SDEV therapy produced the most significant change in Parasympathetic activity, followed by SD, with SDE having the least average effect on Parasympathetic activity. SDEV therapy also produced the most significant change in Sympathetic activity, with SD having essential no effect on Sympathetic activity, and SDE having a depressing effect on Sympathetic activity. The significant increase in Sympathetic activity in response to SDEV, over that in response to SD or SDE, is a result of direct stimulation of the Parasympathetic activity and the feedback relationship

TABLE 4

Resting Baseline Statistical Means Follow-up (Test 2) Responses:

| F/U | Bx LFa | Bx RFa | SB$^{Error! Bookmark not defined.}$ | DB RFa | V LFa | V, PE (%) | PC LFa | PC, PE (%) |
|---|---|---|---|---|---|---|---|---|
| SD | 3.83 | 4.12 | 2.09 | 33.41 | 55.20 | 50.00 | 6.60 | 40.18 |
| SDE | 2.03 | 2.70 | 1.97 | 39.02 | 52.29 | 65.53 | 7.77 | 52.43 |
| SDEV | 4.40 | 3.24 | 3.19 | 23.56 | 50.41 | 44.29 | 4.87 | 38.57 | between the two nervous systems. The other two therapy modalities are indirect, systemic therapies which do not affect the feedback relationship as strongly.

Given the mixed results, consider the SB responses. SDE changed SB most in the direction of increasing relative Parasympathetic activity ($\Delta=-0.02$), SD averaged no (net) change in P&S balance and SDEV changed SB least in the direction of increasing relative Parasympathetic activity ($\Delta=0.95$).

In general, by increasing resting Parasympathetic activity, the (abnormal) dynamic Parasympathetic responses (leading to PE) were reduced. Reducing the dynamic, excess Parasympathetic responses also reduced morbidity risks, apparently including excess levels of pro-inflammatory cytokines within the CNS; thereby improving patient outcomes.

These results indicate that the invention methods provided herein reduce the excess levels of pro-inflammatory cytokines within the CNS; thereby reversing autonomic nervous system damage.

Example 2—the Nemechek Protocol Including Intermittent Fasting

A. Treatment Protocol:

From an autonomic dysfunction perspective, patients most commonly requiring intermittent fasting (IF) are often those who have suffered significant traumatic brain injuries (TBI), as compared to emotional trauma, pregnancy or chronic inflammatory damage. Traumatic brain injuries are more of a challenge to reverse because the physical shearing forces associated with TBI will tear or snap neurons in half whereas this is not known to occur with emotional or inflammatory neuronal disruption. Other patients with obesity, diabetes, sleep apnea, fatty liver disease, intra-abdominal adiposity and organ failure (cardiomyopathy, chronic kidney disease, neurodegenerative disorders) are also placed on an intermittent fasting regimen either for the removal of ectopic adipose or for the cellular reparative effect (i.e. hormesis) that intermittent fasting has on their organs.

All patients (regardless of trauma type) begin with the SDEV regimen, and are informed that a change to their eating routine will be implemented around the 4 month mark. At the 4-6 month mark after initiating Nemechek Protocol SDEV regimen (e.g., being administered antibiotic, DHA supplement and oleic acid in the form of EVOO, and tVNS as described for the SDEV patient group in Example 1), patients are started on a 1:6 intermittent fasting regimen as a long term recommendation and are encouraged to utilize the 2:5 intermittent fasting regimen.

It is believed that patients with higher levels of pro-inflammatory cytokines within the central nervous system or periphery have a slower and potentially incomplete recovery of autonomic function. The addition of intermittent fasting in the Nemechek Protocol invention methods provided herein, after 4 to 6 months of initiating the SDEV regimen, improves the rate and completeness of autonomic damage recovery as measured on spectral analysis, as well as broadens the degree of symptomatic and clinical improvement.

Since many patients with autonomic dysfunction have increased caloric consumption in response to cerebral hypoperfusion, intermittent fasting reduces excessive adiposity especially in ectopic sites such as the intra-abdominal cavity, buttocks and the head and neck.

While the present embodiments have been particularly shown and described with reference to example embodiments herein, it will be understood by those of ordinary skill in the art that various changes in form and details may be made therein without departing from the spirit and scope of the present embodiments as defined by the following claims.

What is claimed is:

1. A method for reducing parasympathetic excess (PE) in a subject in need thereof, comprising:
    administering to said subject rifaximin, wherein rifaximin is administered for 10-14 days; a polyunsaturated omega-3 fatty acid, wherein the polyunsaturated omega-3 fatty acid comprises DHA in a daily concentration range selected from: about 2,000-4,000 mg, or about 3,000 mg; and olive oil, wherein the olive oil is administered daily in an amount selected from: about 5 ml to about 100 ml, about 10 ml to about 75 ml, about 15 ml to about 50 ml, about 20 ml to about 40 ml, or about 25 ml;
    providing VNS (vagal nerve stimulation) to the subject, wherein the VNS is provided transcutaneously using electrical stimulation, wherein the electrical stimulation is achieved by clipping electrodes across the tragus of an ear and inducing an electrical current with a transcutaneous electrical nerve stimulation (TENS) unit; and
    placing said subject on an intermittent fasting regimen, wherein the intermittent fasting regimen comprises fasting for multiple days but not on consecutive days; and
    wherein the prevalence of parasympathetic excess (PE) is decreased.

2. The method claim 1, wherein rifaximin is administered at a dosage of 550 mg, 1 tablet by mouth 2-3 times daily.

3. The method of claim 1, wherein a second antibiotic is administered to the subject.

4. The method of claim 3, wherein the second antibiotic is selected from metronidazole or neomycin.

5. The method of claim 1, wherein the olive oil is extra virgin olive oil.

6. The method of claim 1, wherein the electrical current has a frequency in the range selected from: about 0.1 Hz to about 30 Hz, about 0.3 Hz to about 25 Hz, about 0.5 Hz to about 20 Hz, about 0.7 Hz to about 15 Hz, about 0.9 Hz to about 10 Hz, about 1.0 Hz to about 9 Hz, about 1.2 Hz to about 8 Hz, about 1.4 Hz to about 7 Hz, about 1.6 Hz to about 6 Hz, or about 2 Hz to about 5 Hz; has a pulse width in the range selected from: about 20 to about 1000 uS, about 30 to about 900 uS, about 40 to about 800 uS, about 50 to about 700 uS, about 60 to about 600 uS, about 70 to about 500 uS, about 80 to about 450 uS, about 90 to about 400 uS, about 100 to about 350 uS, about 110 to about 325 uS, about 120 to about 300 uS, about 130 to about 275 uS, about 140 to about 260 uS, or about 150 to about 250 uS; and a current in a range selected from: about 0.1 to about 5.0, about 0.2 to about 4.0, about 0.3 to about 3.0, about 0.4 to about 2.0, or about 0.5 to about 1.0 Amps.

7. The method of claim 6, wherein the electrical current has a frequency at 2-5 Hz, pulse width at 150-250 uS and 0.5-1.0 mAmps.

8. The method of claim 1, wherein the electrical stimulation is used for a time selected from the group consisting of: about 30 minutes up to about 8 hours, about 45 minutes up to about 7 hours, about 1 hour up to about 6 hours, about 1.5 hours up to about 5 hours, and about 2 hours up to about 4 hours; per day.

9. The method of claim 8, wherein the electrical stimulation is used about 2 hours up to about 4 hours per day.

10. The method of claim 1, wherein total dietary caloric intake is reduced to an amount selected from the group consisting of less than 1000, less than 900, less than 800, less than 700, less than 600 or less than 500 calories per fasting-day for women; and less than 1200, less than 1100, less than 1000, less than 900, less than 800, less than 700, or less than 600 calories per fasting-day for men.

11. The method of claim 1, wherein a condition treated herein is selected from the group consisting of: traumatic brain injury, concussion, chronic traumatic encephalopathy (CTE), post-concussion syndrome (PCS), Alzheimer's disease, Parkinson's disease, essential tremor, post-traumatic stress disorder (PTSD), chronic depression, treatment resistant epilepsy, autism, developmental delay and sensory perception disorder.

12. The method of claim 1, wherein a condition treated herein is selected from the group consisting of:
rheumatoid arthritis, appendicitis, peptic, gastric or duodenal ulcers, peritonitis, pancreatitis, ulcerative, pseudomembranous, acute or ischemic colitis, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopicsilicovolcanoconiosis-,
alvealitis, bronchiolitis, pharyngitis, pleurisy, sinusitis, influenza, respiratory syncytial virus, herpes, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis *nodosa*, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, Type I diabetes, ankylosing spondylitis, Berger's disease, Reiter's syndrome, or Hodgkin's disease.

13. The method of claim 1, wherein a condition treated herein is selected from the group consisting of: hay fever, atherosclerosis, rheumatoid arthritis, bursitis, gouty arthritis, polymyalgia rheumatic arthritis, asthma, autoimmune diseases, chronic inflammation, chronic prostatitis, glomerulonephritis, nephritis, inflammatory bowel diseases, pelvic inflammatory disease, reperfusion injury, transplant rejection, vasculitis, myocarditis, and colitis.

14. The method of claim 1, wherein the prevalence of postural change (PC) PE is decreased by approximately 32%.

15. A method for reversing acute and/or chronic autonomic damage in a subject in need thereof, comprising:
administering to said subject an effective amount of an antibiotic; an effective amount of polyunsaturated omega-3 fatty acid; and an effective amount of oleic acid; providing VNS (vagal nerve stimulation) to the subject, and decreasing the prevalence of Valsalva (V) PE by approximately 48%.

* * * * *